United States Patent [19]

Stern

[11] Patent Number: 5,470,231
[45] Date of Patent: Nov. 28, 1995

[54] METHOD OF FORMING PORCELAIN TOOTH RESTORATIONS

[76] Inventor: Alvin L. Stern, P.O. Box 711333, Houston, Tex. 77271-1333

[21] Appl. No.: 230,508

[22] Filed: Apr. 20, 1994

[51] Int. Cl.⁶ .............................. A61C 5/08; A61C 5/10
[52] U.S. Cl. ............................................. 433/223; 433/218
[58] Field of Search ........................... 433/202.1, 217.1, 433/218, 222.1, 223, 228.1

[56] References Cited

U.S. PATENT DOCUMENTS

| | | | |
|---|---|---|---|
| 4,364,731 | 12/1982 | Norling et al. | 433/223 X |
| 4,461,618 | 7/1984 | DeLuca et al. | 433/223 X |
| 4,478,579 | 10/1984 | Fischer et al. | 433/223 X |
| 4,562,882 | 1/1986 | Alleluia | 433/200.1 X |
| 4,579,530 | 4/1986 | McLaughlin | 433/213 X |

*Primary Examiner*—Nicholas D. Lucchesi
*Attorney, Agent, or Firm*—Bill B. Berryhill

[57] ABSTRACT

A method of forming a porcelain tooth restoration from a positive replication of the tooth structure on which the tooth restoration is to be placed. Areas of the replication are coated with a liquid preparation which substantially inhibits moisture absorption by the replication. A slurry of powdered porcelain is applied over the coated area of the replication to form at least a portion of the tooth restoration which is cured and eventually separated from the tooth replication for bonding to the tooth structure.

12 Claims, 1 Drawing Sheet

METHOD OF FORMING PORCELAIN TOOTH RESTORATIONS

BACKGROUND OF THE INVENTION

1. Field of the Invention

The present invention pertains to restoration of teeth. More specifically, the present invention pertains to methods of forming porcelain tooth restorations for dental restoration of worn, damaged or malformed teeth.

2. Description of the Prior Art

There are many methods of restoring or repairing teeth. For several decades, practitioners in the field of restorative dentistry have developed several methods and materials for restoring worn, damaged or malformed teeth with porcelain restorations. Porcelain is attractive and relatively inexpensive. Porcelain restorations may be used for inlays, onlays, crowns and veneers to correct structural and/or cosmetic deficiency of teeth. Such porcelain restorations are custom made for bonding to an underlying or adjacent tooth structure.

In most recent times, there have been two basic methods for producing an all-porcelain restoration: the foil or "indirect" method and the refractory or "direct" method. In the foil method, a mold is made of the tooth structure on which the restoration is to be placed and a positive replication of the tooth structure is formed from a material poured into the mold. Then a platinum foil matrix is applied to and burnished over the tooth structure replication. Then, dental porcelain, in a water-based slurry, is applied over the foil matrix, baked in a furnace, ground and glazed to produce a restoration which can be bonded to the original tooth structure.

Though the foil method of producing a porcelain restoration has been proven, there are problems associated with such a method. Foil, by its nature, is difficult to completely form and adapt to the surface of a tooth structure replication and due to the fact that porcelain must be built up on the foil and must be removed from the tooth replication for subsequent firings and with the final peeling out of the foil from the finished restoration, the porcelain restorations frequently are deficient in accuracy of fit. This requires filling in with other materials so that the tooth restoration may be bonded to the original tooth structure.

The second and more accurate method of producing porcelain restorations requires the use of high heat resistant refractory investment materials molded in the shape of the tooth structure on which the toot restoration is to be placed. The refractory investment replicates the original tooth structure and allows for direct application and subsequent firings of porcelain thereto. This method, referred to as the refractory or "direct" method results in a porcelain restoration with far greater accuracy of fit.

Even though the direct method of producing a porcelain restoration is preferred in the dental industry, there are a number of problems and inconveniences associated therewith. In typical practice, the tooth structure to which the porcelain is to be bonded is replicated with a high heat resistant refractory investment material. The tooth structure replication must undergo a degassing or curing process. Then, before a water-based porcelain mixture can be applied to the tooth structure replication, water must be absorbed into the refractory. If this is not done, the water in the water-based porcelain slurry will be quickly absorbed into the refractory, preventing the porcelain from flowing or being adapted to the surface of the tooth replication.

Even with careful saturation of the refractory tooth replication, problems occur. For example, in U.S. Pat. No. 4,579,530 it is mentioned that the first application of porcelain slurry, after being cured, produces a very cracked surface having, as described in the above referenced patent, the appearance of "a dried-out river bed". This appears to be due to the absorption of water into the refractory tooth replication and subsequent drying thereof. These cracked surfaces then require healing by adding succeeding layers of porcelain.

In addition to resulting in a very cracked surface, the presently used direct method of porcelain tooth restoration requires considerable waiting time (at least four to ten minutes) for water absorption by the tooth replication refractory. Porcelain lifting or peeling problems are also encountered in firing subsequent layers of porcelain. Thus, while this method of forming porcelain restorations is one of the most effective to date, there are improvements which need to be made.

SUMMARY OF THE INVENTION

The present invention provides a method of forming a porcelain tooth restoration which eliminates the water absorption problems associated with the aforementioned direct method. No time is wasted allowing the tooth structure replication or model to absorb water prior to applying restoration materials thereto. Furthermore, when the restoration materials are applied, the tendency to crack in the prior art is eliminated or greatly reduced.

In the method of forming a porcelain tooth restoration of the present invention, a negative impression of the tooth structure on which a tooth restoration is to be placed is prepared and a positive replication of the tooth structure is formed of a porcelain compatible refractory investment material as in the prior art. However, after the positive replication is cured, the areas on and around the area of the replication which is to receive porcelain is coated with a preparation which, in a preferred embodiment, comprises an aqueous colloidal dispersion of silica particles. Although the carrier of such a preparation may be water it may also include other liquids, such as glycol. This coating preparation substantially inhibits the rate of moisture absorption into the refractory material. In effect, it is a moisture absorption barrier. Then a mixture of the coating preparation and powdered porcelain or water-based porcelain may be applied over the coated areas of the replication to form at least a portion of the tooth restoration. The mixture is cured by firing. After firing, additional mixtures of porcelain materials may be applied to finish forming the tooth restoration. After final firing of the tooth restoration, the investment material of the positive replication of the tooth structure may be removed, leaving the tooth restoration for bonding to the tooth structure.

Thus, the method of forming a porcelain tooth restoration of the present invention substantially eliminates the problems associated with water absorption in the methods of the prior art. The method provides a non-water absorbing porcelain application technique which reduces manufacturing time and provides crack-free formation and firing of porcelain. This eliminates having to heal cracks and provides an eventual porcelain restoration which is stronger and more accurate in fit. Many more objects and advantages of the invention will be apparent from reading the description which follows in conjunction with the accompanying drawings.

DESCRIPTION OF A PREFERRED EMBODIMENT OF THE INVENTION

Figure 1:
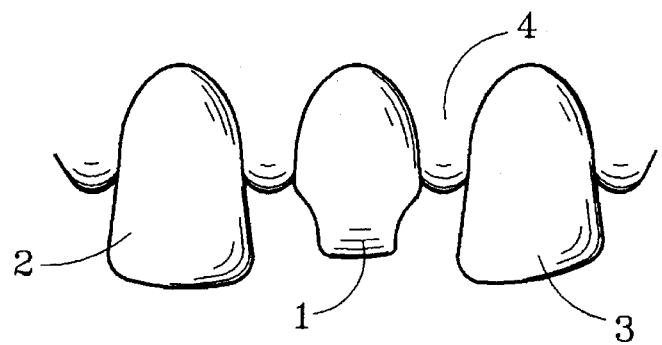
FIG. 1 is a frontal elevation view of a portion of a patient's mouth illustrating three teeth, the middle one of which is in need of restoration.

The present invention provides a method of forming porcelain tooth restorations. Such restorations include items referred to in dental practice as: inlays, onlays, crowns and veneers. The method of the present invention is suitable for forming any such items. However, for purposes of illustration, the method of the present invention will be described in forming a porcelain crown to be placed on a tooth structure 1 illustrated in FIG. 1. In FIG. 1, the tooth structure 1 is illustrated as being between two other teeth 2 and 3 extending from the gum 4 of a patient. It is presumed that the tooth structure 1 has been dentally prepared to receive a tooth restoration (crown) so that the tooth structure 1 and the crown to be placed thereon will approximate the original tooth.

Figure 2:
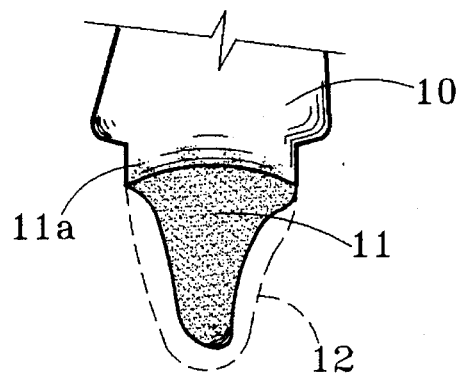
FIG. 2 represents the replication of the tooth structure of the middle tooth of FIG. 1, as viewed from the side thereof.
Figure 3:
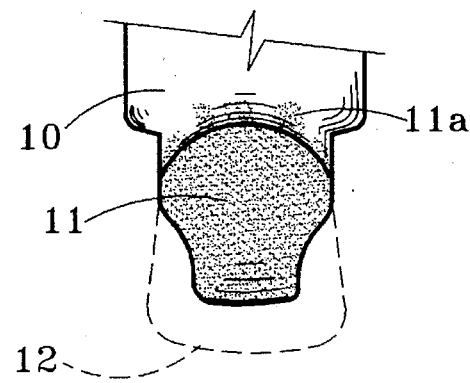
FIG. 3 represents a replication of the middle tooth structure of FIG. 1 as viewed from the front thereof.

The initial step of forming a porcelain restoration in the direct method of the present invention, as well as the prior art, is the preparation of a negative impression of the tooth structure 1 on which a tooth restoration is to be placed. This is accomplished by forming an impression of the tooth utilizing conventional mold material therefor. After the negative impression is prepared a positive replication of the tooth structure 1 is formed in the negative impression with a porcelain compatible refractory investment material of a type which is also well known. The replication material is cured leaving a positive replication 10 such as illustrated in FIGS. 2 and 3 of the drawings. The material which forms the tooth replication 10 is typically a material which easily absorbs water. For this reason, in methods of the prior art, the tooth replication 10 is typically placed in water for a period of time (at least four to ten minutes) to allow it to become saturated with water so that the water from water-based porcelain preparations will not be quickly absorbed thereinto. It is at this point that the method of forming a tooth restoration of the present invention departs substantially from the methods of the prior art.

In the method of the present invention, it is not necessary to soak the tooth replication 10 in water as in the prior art. Instead, the areas of the replication 10 which are to receive restoration materials, those shaded areas indicated by the reference 11 in FIGS. 2 and 3, and the adjoining marginal areas 11a are coated with a liquid preparation which substantially inhibits moisture absorption by the tooth replication 10. In a preferred embodiment, the preparation comprises an aqueous colloidal dispersion of silica particles. While the term "aqueous" normally suggests water, it also means other fluids with similar fluid characteristics. As used herein "aqueous" is used in the broader sense to include not only water but other liquids. In fact, even though the liquid carrier of the coating preparation may be predominantly water, it may also include other components such as glycol or it may be all glycol or some other liquid. It has been found that at least some glycol will improve the flow characteristics of the coating preparation. It also prevents freezing and probably contributes to inhibition of water absorption. The coating preparation is particularly formulated to substantially inhibit the rate of water absorption into the refractory material. In effect, it provides a moisture absorption barrier.

Silica (silicon dioxide) occurs in crystalline, amorphous and impure forms (as in quartz, opal and sand, respectively). The preferred aqueous colloidal dispersion of silicon dioxide would typically include ten to sixty percent, by weight, of silicon dioxide. The aqueous colloidal dispersion may also include, by weight, small amounts of stabilizing substances such as sodium oxide, sodium sulfate, sodium chloride, sodium hydroxide and sodium aluminate. A typical aqueous colloidal dispersion might be ten to sixty percent silicon dioxide, two-tenths to six-tenths percent silica three-hundredths to seven-hundredths percent sodium sulfate and one-hundredth to three-hundredths percent sodium chloride. As previously stated, the aqueous colloidal dispersion may also include glycol in varying amounts but at least enough to prevent the preparation from freezing during normal shipping and handling conditions.

Immediately after coating the areas 11 and 11a of the replication 10 with the previously described preparation, a mixture of the preparation and powdered porcelain may be applied to the coated area 11, as a slurry, to form at least a portion of the tooth restoration. By mixing powdered porcelain with the preparation, the strength of the porcelain appears to be increased. This appears to be due to the silica in the preparation. Alternatively, a purely water-based porcelain slurry may be applied. The replication and t his layer of mixture may then be placed in a porcelain furnace for a typical baking or firing procedure.

After the first firing, additional layers of the preparation and porcelain mixture or conventional water-based porcelain slurry may be applied so as to continue to build up the tooth restoration. During this process, areas 11a adjacent to the restoration material may be coated-with the preparation of the present invention to prevent water absorption into the tooth structure replication 10. The final layers of porcelain mixture may be fired, ground and glazed in a conventional manner to completion. The restoration, in this case a crown, is finally built up to the final shape, as indicated by the dotted lines 12 in FIGS. 2 and 3.

Figure 4:
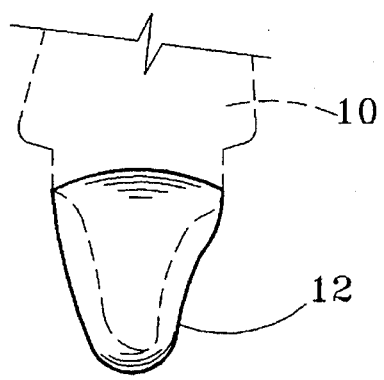
FIG. 4 represents a porcelain tooth restoration formed by the method of the present invention, as viewed from the side thereof.
Figure 5:
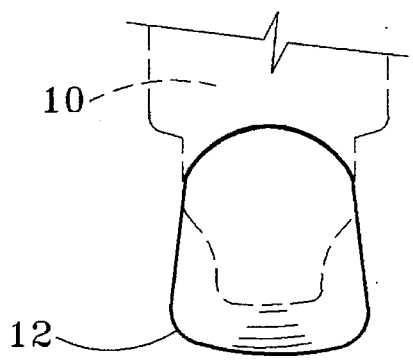
FIG. 5 represents the tooth restoration of FIG. 4 as viewed from the front thereof.

After the restoration is completed, the tooth structure replication 10 (represented by dotted lines in FIGS. 4 and 5) is removed by cutting away, sandblasting, etc. in a conventional manner. This leaves the tooth restoration 12 (as in FIGS. 4 and 5) for placement on and bonding to the tooth structure 1 of FIG. 1. This tooth restoration 12 is a crack free one of superior accuracy, strength and integrity produced much quicker and better than the methods of the prior art.

Although several materials and methods of forming a porcelain tooth restoration of the present invention has been described herein, many variations thereof can be made without departing from the spirit of the invention. Accordingly, it is intended that the scope of the invention be limited only by the claims which follow.

I claim:

1. A method of forming an all porcelain tooth restoration comprising the steps of:

preparing a negative impression of the tooth structure on which a tooth restoration is to be placed;

forming from said negative impression a positive replication of said tooth structure of a porcelain compatible refractory investment material;

coating the areas of said replication which are to receive restoration materials with a liquid preparation which substantially inhibits moisture absorption by said replication;

applying a slurry of powdered porcelain over said coated areas of said replication to form at least a portion of a tooth restoration;

curing said at least a portion of a tooth restoration by firing thereof; and removing said tooth structure replication to leave said at least a portion of a tooth restoration for bonding to said tooth structure.

2. The method of forming a porcelain tooth restoration as set forth in claim 1 in which said liquid preparation comprises an aqueous colloidal dispersion of silica particles.

3. The method of forming a porcelain tooth restoration as set forth in claim 2 in which said aqueous colloidal dispersion comprises, by weight, ten to sixty percent silica.

4. The method of forming a porcelain tooth restoration as set forth in claim 3 in which said aqueous colloidal dispersion comprises, by weight, approximately one percent or less of one or more of the following stabilizing substances: sodium oxide, sodium sulfate, sodium chloride, sodium hydroxide and sodium aluminate.

5. The method of forming a porcelain tooth restoration as set forth in claim 1 in which said liquid preparation includes enough glycol to prevent said preparation from freezing under normal shipping and handling conditions.

6. The method of forming a porcelain tooth restoration as set forth in claim 1 in which water based porcelain slurry is applied to said at least a portion of a tooth restoration to form a complete tooth restoration; said complete tooth restoration being fired again before removing said replication investment material.

7. The method of claim 1 in which the marginal areas of said replication adjacent the areas which are to receive said restoration materials are also coated with said liquid preparation.

8. The method of claim 1 in which said preparation comprises water and silica.

9. The method of claim 8 in which the silica in said preparation when mixed with said powdered porcelain is sufficient to substantially increase the strength of the porcelain after firing.

10. The method of claim 1 in which said preparation comprises water and glycol.

11. The method of claim 1 in which said slurry of powdered porcelain comprises a mixture of said liquid preparation and powdered porcelain.

12. The method of claim 11 in which purely water-based porcelain slurry is applied to said at least a portion of a tooth restoration to form a complete tooth restoration, said complete tooth restoration being fired again before removing said replication investment material.

* * * * *